United States Patent
Bonutti et al.

(10) Patent No.: US 9,883,883 B2
(45) Date of Patent: Feb. 6, 2018

(54) ULTRASONIC HANDPIECE

(75) Inventors: Peter M. Bonutti, Effingham, IL (US);
Justin Beyers, Effingham, IL (US);
Matthew Cremens, Effingham, IL (US); Frank Anthony Crandall, Salt Lake City, UT (US)

(73) Assignee: P Tech, LLC, Effingham, IL (US)

( * ) Notice: Subject to any disclaimer, the term of this patent is extended or adjusted under 35 U.S.C. 154(b) by 545 days.

(21) Appl. No.: 13/495,728

(22) Filed: Jun. 13, 2012

(65) Prior Publication Data

US 2012/0316472 A1 Dec. 13, 2012

Related U.S. Application Data

(60) Provisional application No. 61/496,147, filed on Jun. 13, 2011, provisional application No. 61/526,182, filed on Aug. 22, 2011, provisional application No. 61/526,207, filed on Aug. 22, 2011.

(51) Int. Cl.
*A61B 17/00* (2006.01)
*A61B 17/32* (2006.01)
*A61B 90/00* (2016.01)

(52) U.S. Cl.
CPC ........... *A61B 17/320068* (2013.01); *A61B 2017/00022* (2013.01); *A61B 2090/064* (2016.02)

(58) Field of Classification Search
None
See application file for complete search history.

(56) References Cited

U.S. PATENT DOCUMENTS

| | | | |
|---|---|---|---|
| 4,027,559 A * | 6/1977 | Wallrafen | 81/57.38 |
| 4,651,716 A | 3/1987 | Forester et al. | |
| 4,750,902 A | 6/1988 | Wuchinich et al. | |
| 5,242,385 A | 9/1993 | Strukel | |
| 5,391,144 A * | 2/1995 | Sakurai et al. | 604/22 |
| 5,514,086 A | 5/1996 | Parisi et al. | |
| 5,674,235 A | 10/1997 | Parisi | |
| 5,796,007 A * | 8/1998 | Panagotopulos et al. | 73/716 |
| 5,897,569 A * | 4/1999 | Kellogg et al. | 606/169 |
| 5,938,677 A | 8/1999 | Boukhny et al. | |
| 5,968,060 A * | 10/1999 | Kellogg | 606/169 |
| 5,997,533 A | 12/1999 | Kuhns | |
| 6,017,354 A * | 1/2000 | Culp et al. | 606/170 |
| 6,028,387 A | 2/2000 | Boukhny et al. | |
| 6,053,906 A | 4/2000 | Honda et al. | |
| 6,217,591 B1 * | 4/2001 | Egan et al. | 606/144 |
| 6,352,532 B1 | 3/2002 | Kramer et al. | |
| 6,425,865 B1 * | 7/2002 | Salcudean | A61B 8/0875 600/111 |
| 6,475,215 B1 | 11/2002 | Tanrisever | |

(Continued)

OTHER PUBLICATIONS

Non-Final Office Action dated Jan. 5, 2015 relating to U.S. Appl. No. 13/495,735, 28 pages.

(Continued)

*Primary Examiner* — Tse Chen
*Assistant Examiner* — Joanne Hoffman

(57) ABSTRACT

An ultrasonic handpiece includes a horn and a transducer system. The transducer system is configured to detect a first pressure applied to at least a first portion of the transducer system, transmit a signal associated with the first pressure, and generate ultrasonic vibratory energy. The first pressure is associated with a second pressure applied to the horn.

6 Claims, 4 Drawing Sheets

(56) References Cited

U.S. PATENT DOCUMENTS

| | | | |
|---|---|---|---|
| 6,494,095 | B1 | 12/2002 | Wan |
| 6,602,193 | B2 | 8/2003 | Chon |
| 6,678,621 | B2 | 1/2004 | Wiener et al. |
| 6,679,899 | B2 | 1/2004 | Wiener et al. |
| 6,817,973 | B2 | 11/2004 | Merril et al. |
| 7,063,692 | B2 | 6/2006 | Sakurai et al. |
| 7,235,072 | B2 | 6/2007 | Sartor et al. |
| 7,273,483 | B2 | 9/2007 | Wiener et al. |
| 7,313,949 | B2 * | 1/2008 | Yorita et al. ............... 73/114.07 |
| 7,476,233 | B1 | 1/2009 | Wiener et al. |
| 7,758,547 | B2 * | 7/2010 | Tonelli ............... A61M 1/3672 |
| | | | 222/333 |
| 7,776,027 | B2 | 8/2010 | Manna et al. |
| 8,057,480 | B2 | 11/2011 | Dorawa et al. |
| 2002/0049464 | A1 * | 4/2002 | Donofrio et al. ............. 606/169 |
| 2004/0010222 | A1 * | 1/2004 | Nunomura ............ A61B 17/54 |
| | | | 604/22 |
| 2004/0115591 | A1 | 6/2004 | Warner |
| 2004/0211260 | A1 | 10/2004 | Girmonsky et al. |
| 2004/0267134 | A1 | 12/2004 | Hossack et al. |
| 2005/0288659 | A1 | 12/2005 | Kimura et al. |
| 2006/0229514 | A1 | 10/2006 | Wiener |
| 2006/0235424 | A1 * | 10/2006 | Vitale et al. ................... 606/90 |
| 2007/0016235 | A1 | 1/2007 | Tanaka et al. |
| 2007/0031780 | A1 | 2/2007 | Warner et al. |
| 2007/0083209 | A1 * | 4/2007 | Schenberger et al. .......... 606/82 |
| 2007/0123769 | A1 * | 5/2007 | Fuller et al. .................. 600/405 |
| 2007/0196784 | A1 | 8/2007 | Bochi |
| 2008/0014627 | A1 * | 1/2008 | Merchant .......... A61M 37/0092 |
| | | | 435/259 |
| 2008/0039845 | A1 | 2/2008 | Bonutti et al. |
| 2008/0103515 | A1 | 5/2008 | Wiener |
| 2009/0024161 | A1 * | 1/2009 | Bonutti et al. ................ 606/213 |
| 2009/0036913 | A1 | 2/2009 | Wiener et al. |
| 2009/0098507 | A1 | 4/2009 | Kirstgen |
| 2009/0124585 | A1 | 5/2009 | Cross et al. |
| 2009/0222037 | A1 | 9/2009 | Babaev et al. |
| 2009/0275864 | A1 * | 11/2009 | Hirai ................................ 601/2 |
| 2010/0004585 | A1 | 1/2010 | Boukhny et al. |
| 2010/0004586 | A1 | 1/2010 | Boukhny et al. |
| 2010/0094321 | A1 | 4/2010 | Akahoshi et al. |
| 2010/0174336 | A1 * | 7/2010 | Stein ................. A61N 1/36564 |
| | | | 607/23 |
| 2015/0099966 | A1 * | 4/2015 | Young ................. A61M 5/1452 |
| | | | 600/424 |

OTHER PUBLICATIONS

Non-Final Office Action dated Dec. 19, 2014 relating to U.S. Appl. No. 13/495,742, 26 pages.

Non-Final Office Action dated Apr. 28, 2015 relating to U.S. Appl. No. 13/495,742, 14 pages.

Non-Final Office Action dated May 6, 2015 relating to U.S. Appl. No. 13/495,735, 20 pages.

Office Action from related U.S. Appl. No. 13/495,742, filed Jun. 13, 2012; dated Sep. 28, 2015.

Non-Final Office Action for U.S. Appl. No. 13/495,735, dated Nov. 2, 2015, 19 pages.

Final Office Action dated Feb. 11, 2016 relating to U.S. Appl. No. 13/495,742, 17 pages.

Non-Final Office Action for U.S. Appl. No. 13/495,742, dated Aug. 25, 2016, 17 pages.

Non-Final Office Action for U.S. Appl. No. 13/495,742, dated Mar. 10, 2017, 20 pages.

* cited by examiner

ULTRASONIC HANDPIECE

CROSS REFERENCE TO RELATED APPLICATIONS

This application claims priority to U.S. Provisional Patent Application No. 61/496,147 filed Jun. 13, 2011, U.S. Provisional Patent Application No. 61/526,182 filed Aug. 22, 2011, and U.S. Provisional Patent Application No. 61/526,207 filed Aug. 22, 2011, which are hereby incorporated by reference in their respective entireties.

BACKGROUND

The present disclosure relates generally to medical devices and, more particularly, to an ultrasonic handpiece.

Various types of known medical procedures involve repair and stabilization of body tissue. Such medical procedures may be utilized, for example, to treat conditions, such as, without limitation, a defect, damage, or fracture to bone, damaged or torn muscle, ligament or tendon, or separation of body tissues, etc. For example, fractured bones often involve stabilization of the bone in order to promote healing. Different bones and/or different types of fractures generally require unique procedures and/or surgical implements to facilitate stabilization of the body tissue. Accordingly, medical personnel employ a variety of surgical implements, such as screws, plates, and rods, to stabilize the bone across the fracture. In another example, further surgical implements may be used to anchor torn ligaments or tendons to other appropriate body tissue. As such, a variety of medical procedures and surgical implements are known to be used within the body of a patient to facilitate repair, stabilization, and/or healing of body tissue.

BRIEF SUMMARY

In one aspect, a method is provided for operating a handheld medical device. The method includes detecting a first pressure applied to a force determining mechanism. The first pressure is associated with a second pressure applied to a horn. The method further includes transmitting a signal associated with the first pressure, and generating vibratory energy based at least in part on the first pressure.

In another aspect, a medical device is provided. The medical device includes a vibrating mechanism, a horn, and a force determining mechanism. The vibrating mechanism is configured to generate vibratory energy. The horn is configured to transmit the vibratory energy generated by the vibrating mechanism to an operative site. The force determining mechanism is configured to detect a first pressure applied to the force determining mechanism and transmit a signal associated with the first pressure. The first pressure is associated with a second pressure applied to the horn.

In yet another aspect, an ultrasonic handpiece is provided. The ultrasonic handpiece includes a horn and a transducer system. The transducer system is configured to detect a first pressure applied to at least a first portion of the transducer system, transmit a signal associated with the first pressure, and generate ultrasonic vibratory energy. The first pressure is associated with a second pressure applied to the horn.

The features, functions, and advantages described herein may be achieved independently in various embodiments of the present disclosure or may be combined in yet other embodiments, further details of which may be seen with reference to the following description and drawings.

BRIEF DESCRIPTION OF THE DRAWINGS

FIG. 1 is a schematic illustration of an exemplary surgical system;

FIG. 2 is a cross-sectional view of an exemplary ultrasonic handpiece that may be used with the surgical system shown in FIG. 1;

FIG. 3 is a flowchart of an exemplary method of operating the surgical system shown in FIG. 1; and FIG. 4 is a cross-sectional view of another exemplary ultrasonic handpiece that may be used with the surgical system shown in FIG. 1.

Although specific features of various embodiments may be shown in some drawings and not in others, this is for convenience only. Any feature of any drawing may be referenced and/or claimed in combination with any feature of any other drawing.

DETAILED DESCRIPTION

The present disclosure relates generally to medical devices and, more particularly, to ultrasonic handpieces. In one embodiment, an ultrasonic handpiece includes a vibrating mechanism, a horn, and a force determining mechanism. The force determining mechanism detects a force and/or pressure applied to the force determining mechanism, and transmits a first signal associated with the force and/or pressure to a surgical generator. The surgical generator transmits a second signal to the vibrating mechanism based on the first signal to generate vibratory energy, which is transmitted by the horn to an operative site.

As used herein, an element or step recited in the singular and preceded with the word "a" or "an" should be understood as not excluding plural elements or steps unless such exclusion is explicitly recited. Moreover, references to "one embodiment" and/or the "exemplary embodiment" are not intended to be interpreted as excluding the existence of additional embodiments that also incorporate the recited features.

Figure 1:
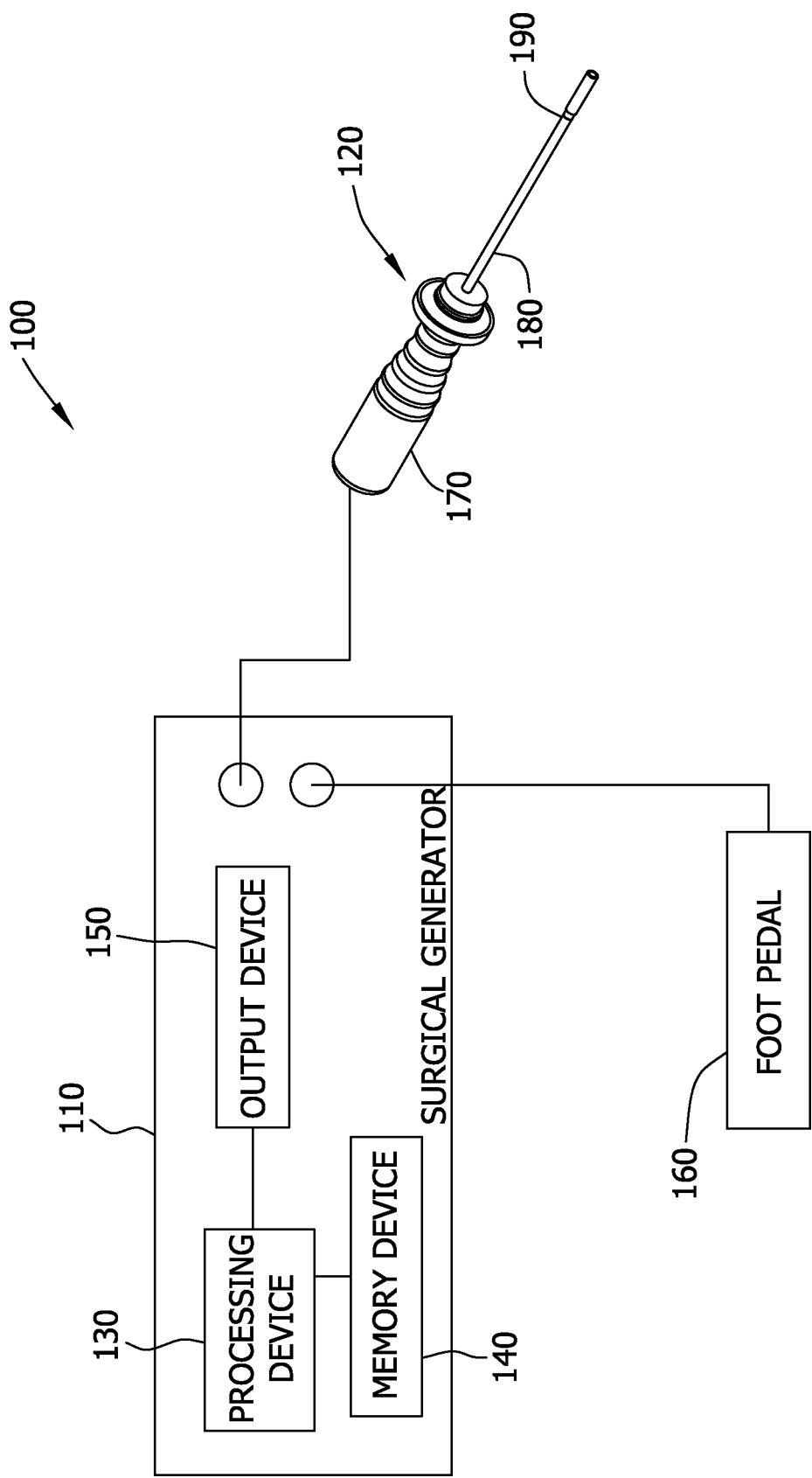
FIGS. 1-4 show exemplary embodiments of the methods and systems described herein.

FIG. 1 shows an exemplary surgical system 100 including a surgical generator 110 and a handpiece 120, which may be removably coupled to surgical generator 110. Alternatively, surgical generator 110 may be integrated with handpiece 120. As used herein, surgical and/or surgery are used to generally refer to any medical procedure involving a patient (a human being, an animal, etc.) and may include in-patient procedures, out-patient procedures, invasive procedures, non-invasive procedures, and/or minimally invasive procedures. In at least some embodiments, surgical implements (not shown) are disposed within the patient's body in orientations suitable for a respective medical procedure, such as a fracture stabilization procedure. Surgical implements may include implants or other suitable medical devices such as, without limitation, pins, screws, fasteners, dowels, rods, plates, and/or anchors. Moreover, as used herein, handpiece is used to generally refer to a housing, casing, frame, holder, and/or support that can be manually carried and manipulated during a medical procedure involving a patient.

In the exemplary embodiment, surgical generator 110 includes a processing device 130 and a memory device 140 coupled to processing device 130. Processing device 130 may include, without limitation, a microcontroller, a microprocessor, a programmable gate array, an application specific integrated circuit (ASIC), a logic circuit, and/or any other circuit, integrated or otherwise, suitable to perform as described herein. Memory device 140 includes one or more devices operable to enable information such as executable instructions and/or other data to be stored and/or retrieved. Memory device 140 may include one or more computer readable media including, without limitation, hard disk storage, optical drive/disk storage, removable disk storage, flash memory, non-volatile memory, ROM, electrically-erasable programmable read-only memory (EEPROM), and/or random access memory (RAM). Memory device 140 is used to store one or more of predetermined thresholds, resonant frequencies, settings specific to handpiece 120, and/or executable instructions.

In the exemplary embodiment, surgical generator 110 includes an output device 150 for example, a cathode ray tube (CRT), a liquid crystal display (LCD), an LED display, an "electronic ink" display, and/or other device suitable to display information to an operator. Additionally, output device 150 may include an audio output device (e.g., a speaker, etc.) to indicate verbal instructions, alerts, and/or warnings to the operator.

In the exemplary embodiment, surgical generator 110 includes one or more input devices, such as, without limitation, a button, a pedal, a knob, a keypad, a pointing device, a mouse, a touch sensitive panel (e.g., a touch pad or a touchscreen), a gyroscope, a position detector, and/or an audio input (e.g., a microphone). For example, in the exemplary embodiment, a foot pedal 160 is removably coupled to surgical generator 110 to enable an operator to provide input to surgical generator 110. In one embodiment, the input device is integrated with surgical generator 110. In another embodiment, the input device is remote from surgical generator 110 and coupled thereto.

Different types of handpieces 120 may be used with surgical generator 110 based on a type of medical procedure and/or a type of surgical implement. For example, various handpieces 120 may have different configurations and/or properties (e.g., acoustical characteristics, resonance frequency), and/or various surgical implements may require handpieces 120 of different sizes and/or configurations. In the exemplary embodiment, an identifier (not shown) enables surgical generator 110 to automatically identify handpiece 120. For example, surgical generator 110 may read and/or detect a resistance identification, an RFID tag, and/or another identifying component to differentiate handpiece 120 from other handpieces 120. Additionally or alternatively, an operator may manually identify handpiece 120. In at least some embodiments, the identifier is associated with multiple medical procedures and/or surgical implements. In such embodiments, the operator may provide, and surgical generator 110 may receive, one or more inputs to select a medical procedure to be performed and/or a surgical implement to be interfaced.

In this manner, one or more handpieces 120 may be replaced between medical procedures. In at least some embodiments, handpiece 120 is removed after each patient such that handpiece 120 may be autoclaved between medical procedures to substantially ensure sterility for one or more subsequent patients. Accordingly, handpiece 120 is configured to withstand multiple autoclave procedures.

In the exemplary embodiment, handpiece 120 includes an outer housing 170, a horn 180 extending longitudinally from outer housing 170, an end effector 190 coupled to horn 180, and a sheath 195 (shown in FIG. 2) coupled to outer housing 170 and extending about and spaced radially from horn 180 and/or end effector 190. In the exemplary embodiment, horn 180 and/or end effector 190 are sized and/or configured to slide within sheath 195. In at least some embodiments, end effector 190 is integrated with horn 180.

In the exemplary embodiment, handpiece 120 is useable to affect one or multiple surgical implements during a surgery. More specifically, handpiece 120 applies vibratory energy, such as ultrasonic energy, to one or more of the surgical implements to form a weld between the surgical implements. Alternatively, handpiece 120 may apply any energy that enables surgical generator 110 and/or handpiece 120 to function as described herein.

In the exemplary embodiment, handpiece 120 is configured to provide an ergonomic interaction with an operator including, without limitation, a surgeon, a doctor, a surgery assistant, a nurse, a veterinarian, and/or other medical personnel present for a medical procedure. Other shapes and/or sizes of handpiece 120 may be included in other surgical system embodiments. In at least some embodiments, handpiece 120 is configured to interact with and/or be utilized by a robotic and/or haptic arm for robotic (e.g., fully automatic or programmed) and/or remote control (e.g., direct human control with end points or boundaries) of handpiece 120.

Figure 2:
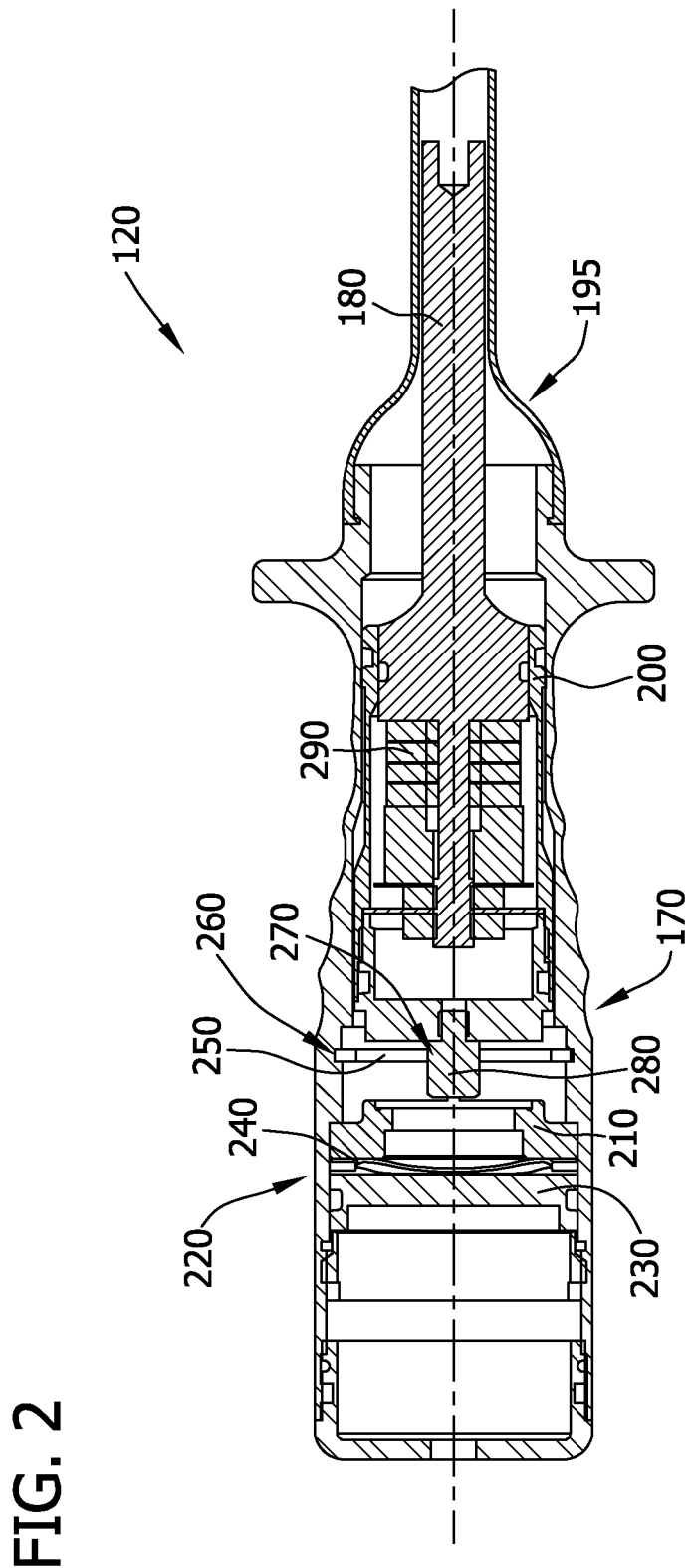

FIG. 2 is a cross-sectional view of handpiece 120. In the exemplary embodiment, outer housing 170 houses at least an inner housing 200 and at least a portion of a transducer system or, more specifically, load cell 210. In the exemplary embodiment, load cell 210 is configured to detect a first force and/or pressure applied to load cell 210 and transmit to surgical generator 110 (shown in FIG. 1) a pressure signal associated with and/or indicative of the first pressure. The first pressure is associated with a force and/or pressure between end effector 190 (shown in FIG. 1) and a surgical implement in contact with end effector 190, which, in turn, directly applies a force and/or pressure to horn 180.

In the exemplary embodiment, a biasing mechanism 220 is positioned within outer housing 170 to counteract, reduce and/or limit the first pressure applied to load cell 210. More specifically, biasing mechanism 220 is moveable between an unflexed or home position and a flexed position. In this manner, load cell 210 "floats" within outer housing 170. As the first pressure applied to load cell 210 generally increases, in the exemplary embodiment, biasing mechanism 220 moves toward the flexed position. Conversely, as the first pressure applied to load cell 210 generally decreases, in the exemplary embodiment, biasing mechanism 220 moves toward the home position. In the exemplary embodiment, biasing mechanism 220 includes a spring plate 230 and a wave spring 240 that is configured to compress as the first pressure increases and/or expand as the first pressure decreases. Alternatively, any type of biasing mechanism 220 may be used that enables handpiece 120 to function as described herein. In at least some embodiments, load cell 210 is fixedly coupled within outer housing 170.

In the exemplary embodiment, outer housing 170 defines a cavity therein that is sized and/or configured such that inner housing 200 is retained within outer housing 170. More specifically, outer housing 170 and/or inner housing 200 includes at least one retaining mechanism 250 that facilitates counteracting, reducing, and/or limiting the first pressure applied to load cell 210. For example, in the exemplary embodiment, retaining mechanism 250 is positioned within outer housing 170 between inner housing 200 and load cell 210 to prevent and/or limit inner housing 200 from moving toward load cell 210 beyond a predetermined position. In the exemplary embodiment, a portion of retaining mechanism 250 is positioned at the predetermined position within a groove 260 defined by an inner surface of outer housing 170. In the exemplary embodiment, retaining mechanism 250 includes an opening 270 extending longitudinally therethrough, and a standoff 280 coupled to inner housing 200 extends through opening 270 such that standoff 280 is configured to directly apply the first pressure to load cell 210. In at least some embodiments, standoff 280 may be a spring. Alternatively, any type of retaining mechanism 250 and/or standoff 280 may be used that enables handpiece 120 to function as described herein.

In the exemplary embodiment, inner housing 200 houses at least a portion of horn 180 and at least a portion of the transducer system or, more specifically, vibrating mechanism 290 coupled to horn 180. In the exemplary embodiment, vibrating mechanism 290 is a piezoelectric stack that is configured to generate vibratory energy (e.g., ultrasonic energy) upon receiving a control signal to activate a weld cycle. In the exemplary embodiment, horn 180 is configured to transmit the vibratory energy to an operative site. More specifically, horn 180 is coupleable to end effector 190 such that the vibratory energy is transmitted to end effector 190 through horn 180. Alternatively, the vibratory energy may be transmitted to the operative site using any mechanism that enables handpiece 120 to function as described herein.

The transducer system includes at least vibrating mechanism 290 and load cell 210. In this manner, the transducer system is configured to detect the first pressure, transmit the pressure signal, and generate ultrasonic vibratory energy. In the exemplary embodiment, vibrating mechanism 290 is remote from load cell 210. Alternatively, vibrating mechanism 290 may be adjacent and/or integrated with load cell 210, or load cell 210 may be adjacent and/or integrated with vibrating mechanism 290. For example, the first pressure may be determined based on a pressure detected by vibrating mechanism 290, and/or load cell 210 may be configured to generate vibratory energy.

In at least some embodiments, handpiece 120 includes a series of electrical contacts that are coupled to vibrating mechanism 290. In such embodiments, the electrical contacts are moveable between a closed configuration and an open configuration such that the electrical contacts are electrically and/or communicatively coupled and/or decoupled, respectively. In such embodiments, as pressure applied to end effector 190, horn 180, and/or load cell 210 generally increases, the electrical contacts move toward the closed configuration, thereby coupling surgical generator 110 to vibrating mechanism 290. Conversely, as pressure applied to end effector 190, horn 180, and/or load cell 210 generally decreases, in such embodiments, the electrical contacts move toward the open configuration, thereby decoupling surgical generator 110 from vibrating mechanism 290. Alternatively, the electrical contacts may be positioned anywhere within handpiece 120 that enables surgical system 100 to function as described herein.

Figure 3:
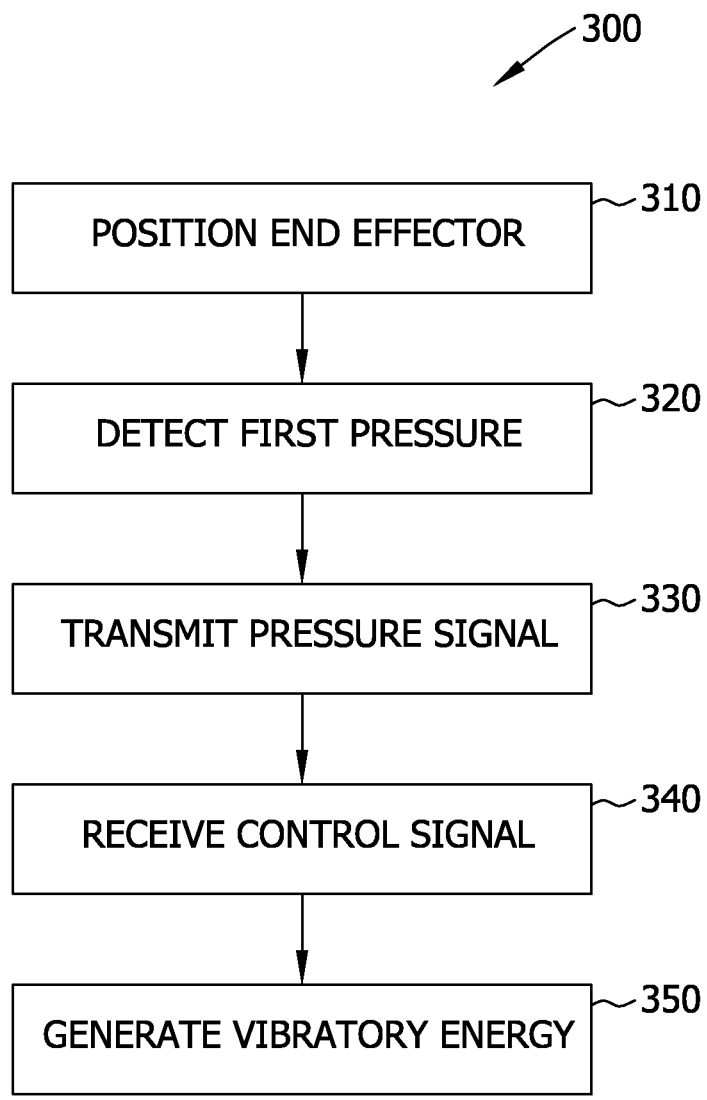

FIG. 3 is a flowchart of an exemplary method 300 of operating surgical system 100. During operation, in the exemplary embodiment, handpiece 120 is identified based on an identifier and/or selected based on a type of medical procedure and/or surgical implement. In the exemplary embodiment, surgical generator 110 retrieves one or more settings associated with handpiece 120, the medical procedure, and/or the surgical implement from memory device 140 based on the identifier. The settings are used by surgical generator 110 to provide one or more control signals to handpiece 120. Settings retrieved from memory device 140 may include, without limitation, frequencies, voltages, currents, and/or control algorithms. For example, in the exemplary embodiment, the setting retrieved from memory device 140 includes a predetermined first force and/or pressure range that enables vibratory energy transfer to the surgical implement, as described below.

Upon identification and/or selection of handpiece 120 and retrieval of one or more settings from memory device 140, surgical system 100 is generally ready to affect the surgical implement. In the exemplary embodiment, end effector 190 is positioned 310 at least partially within the patient and in contact with the surgical implement. More specifically, the operator uses handpiece 120 to apply force and/or pressure to the surgical implement, which, in turn, applies a force and/or pressure to horn 180 and inner housing 200. As a result, standoff 280 applies the first pressure to load cell 210, which detects 320 the first pressure and transmits 330 the pressure signal from handpiece 120 to surgical generator 110.

In at least some embodiments, output device 150 presents an indication of the pressure to the operator. For example, in one embodiment, a visual display presents a visual indication of the applied pressure relative to the first pressure range such that the operator is able to visualize what, if any, corrections need to be made in order to provide a pressure within the first pressure range. Additionally or alternatively, an audio output device presents an audible tone indicative of the applied pressure, and/or a tactile output device presents vibrations indicative of the applied pressure. The tone and/or vibrations may include three rates, volumes, and/or intensities: a first rate, volume, and/or intensity indicating the pressure is below the first pressure range, a second rate, volume, and/or intensity indicating the pressure is within the first pressure range, and a third rate, volume, and/or intensity indicating the pressure is above the first pressure range. As such, the audible tone and/or the vibrations enable the operator to understand the applied pressure relative to the first pressure range without diverting the operator's visual attention from the patient and/or surgical implement.

In the exemplary embodiment, when the pressure is below the first pressure range, output device 150 presents no visual or audible indicator. When the pressure is within the first pressure range, output device 150 presents a ready light and a beep that is emitted at one second intervals. When the pressure is above the first pressure range, output device 150 presents an "over pressure" display and a beep that is emitted at half-second intervals. Alternatively, output device 150 may present any indication to the operator that enables surgical system 100 to function as described herein.

In the exemplary embodiment, when the applied pressure is within the predetermined pressure range, the operator presses foot pedal 160 down to initiate transmission of the control signal to activate a weld cycle. More specifically, surgical generator 110 transmits the control signal to handpiece 120 upon determining and/or identifying that the applied pressure is within the first pressure range and/or determining and/or identifying that foot pedal 160 is pressed down. In one embodiment, the control signal is transmitted to handpiece 120 upon receiving the first indication that the applied pressure is within the first pressure range and then the second indication that foot pedal 160 is pressed second. In another embodiment, the control signal is transmitted to handpiece 120 upon receiving the second indication that foot pedal 160 is pressed down and then the first indication that the applied pressure is within the first pressure range.

In the exemplary embodiment, vibrating mechanism 290 receives 340 the control signal to activate a weld cycle and generates 350 vibratory energy upon receiving the control signal. The vibratory energy is transferred through horn 180 and end effector 190 to the surgical implement. The vibratory energy propagates through the surgical implement to vibrate the surgical implement and an adjacent surgical implement, which generates heat and a weld therebetween.

During operation of handpiece 120 in the active weld cycle, output device 150 presents an indication of the active weld cycle to the operator. For example, in one embodiment, an audio output device presents an audible tone indicative of the active weld cycle. In the exemplary embodiment, the active weld cycle stops when the weld is complete. More specifically, surgical generator 110 determines and/or identifies that the weld is complete based on a predetermined amount of energy or work applied by handpiece 120, and stops transmission of the control signal and/or transmits a second control signal to stop the active weld cycle when the weld is complete. In the exemplary embodiment, the amount of energy applied to the surgical implement is approximately 100 Joules (J). Alternatively, surgical generator 110 may apply any amount of energy that enables surgical system 100 to function as described herein.

Figure 4:
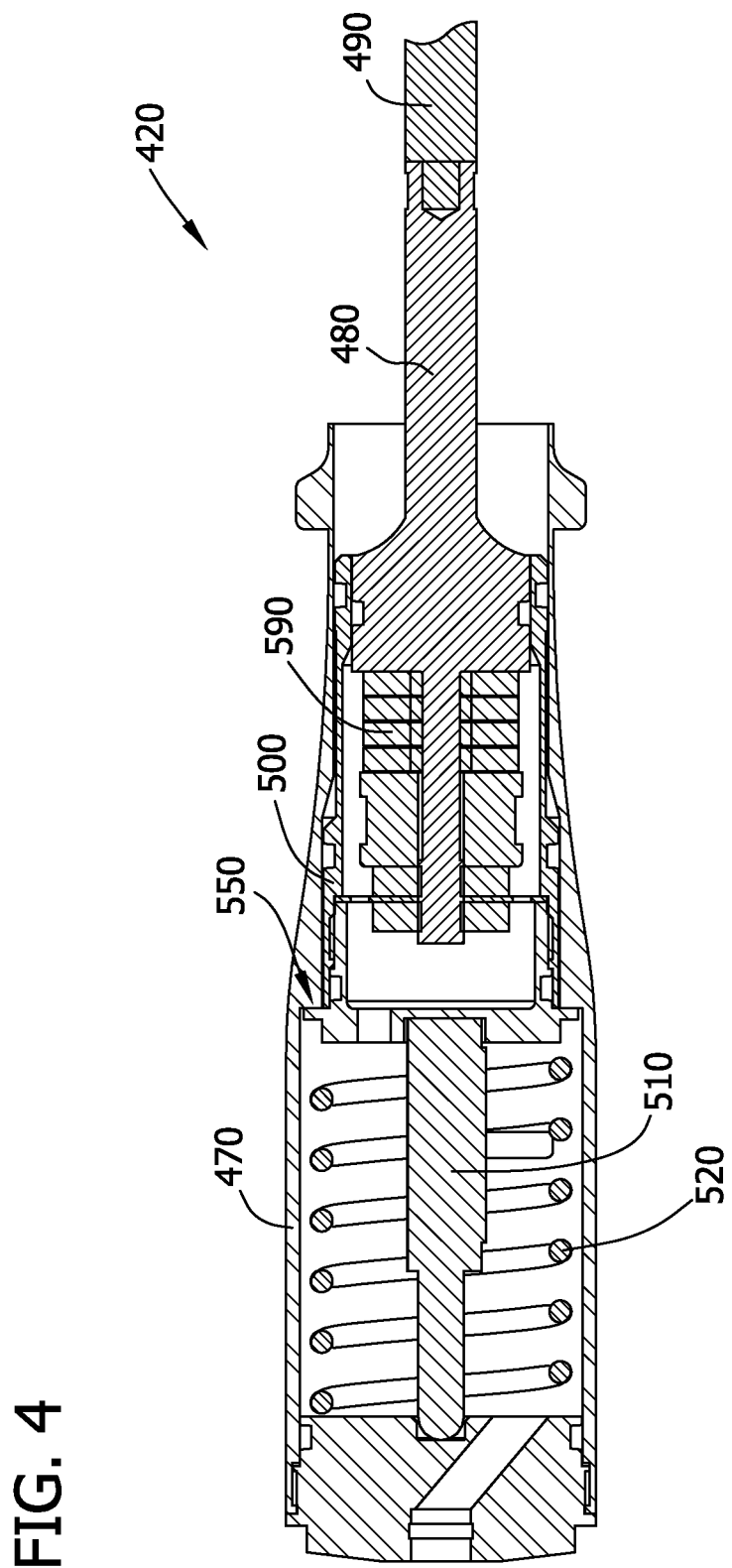

FIG. 4 is a cross-sectional view of another exemplary handpiece 420, which may be removably coupled to surgical generator 110 (shown in FIG. 1). Alternatively, surgical generator 110 may be integrated with handpiece 420. In the exemplary embodiment, handpiece 420 includes an outer housing 470, a horn 480 extending longitudinally from outer housing 470, an end effector 490 coupled to horn 480, and a sheath (not shown) coupled to outer housing 470 and extending about and spaced radially from horn 480 and/or end effector 490. In the exemplary embodiment, horn 480 and/or end effector 490 are sized and/or configured to slide within the sheath. In at least some embodiments, end effector 490 is integrated with horn 480.

In the exemplary embodiment, handpiece 420 is useable to affect one or multiple surgical implements during a surgery. More specifically, handpiece 420 applies vibratory energy, such as ultrasonic energy, to one or more of the surgical implements to form a weld between the surgical implements. Alternatively, handpiece 420 may apply any energy that enables surgical generator 110 and/or handpiece 420 to function as described herein.

In the exemplary embodiment, handpiece 420 is configured to provide an ergonomic interaction with the operator. Other shapes and/or sizes of handpiece 420 may be included in other surgical system embodiments. In at least some embodiments, handpiece 420 is configured to interact with and/or be utilized by a robotic arm for robotic and/or remote control of handpiece 420.

In the exemplary embodiment, outer housing 470 houses at least an inner housing 500, a positional sensor 510 extending longitudinally or axially between an end cap of inner housing 500 and an end cap of outer housing 470, and a biasing mechanism 520 moveable between an unflexed or home position and a flexed position. As a first force and/or pressure applied to positional sensor 510 and/or biasing mechanism 520 generally increases, in the exemplary embodiment, biasing mechanism 520 moves toward the flexed position. Conversely, as the first pressure applied to positional sensor 510 and/or biasing mechanism 520 generally decreases, in the exemplary embodiment, biasing mechanism 520 moves toward the home position.

In the exemplary embodiment, the first pressure is associated with a force and/or pressure between end effector 490 and a surgical implement in contact with end effector 490, which, in turn, directly applies a force and/or pressure to horn 480. In the exemplary embodiment, biasing mechanism 520 is a coil spring configured to compress as the first pressure increases and/or expand as the first pressure decreases. Alternatively, any type of biasing mechanism 520 may be used that enables handpiece 420 to function as described herein.

In the exemplary embodiment, positional sensor 510 is configured to detect the first pressure applied to positional sensor 510 and/or biasing mechanism 520 and transmit to surgical generator 110 a pressure signal associated with and/or indicative of the first pressure. More specifically, positional sensor 510 detects a longitudinal or axial compression and/or extension of positional sensor 510 and/or biasing mechanism 520 and determines the first pressure based at least in part on the axial compression and/or extension. In the exemplary embodiment, positional sensor 510 is a linear variable differential transformer and/or a Hall effect sensor. Alternatively, positional sensor 510 may be any sensor that enables handpiece 420 to function as described herein.

In the exemplary embodiment, outer housing 470 defines a cavity therein that is sized and/or configured such that inner housing 500 is retained within outer housing 470. More specifically, outer housing 470 and/or inner housing 500 includes at least one retaining mechanism 550 configured to prevent and/or limit inner housing 500 from moving away from positional sensor 510 and/or biasing mechanism 520 beyond a predetermined position. In the exemplary embodiment, retaining mechanism 550 is a step that generally complements a flange extending radially outward from the end cap of inner housing 500. Alternatively, any type of retaining mechanism 550 may be used that enables handpiece 420 to function as described herein.

In the exemplary embodiment, inner housing 500 houses at least a portion of horn 480 and at least a portion of the transducer system or, more specifically, vibrating mechanism 590 coupled to horn 480. In the exemplary embodiment, vibrating mechanism 590 is a piezoelectric stack that is configured to generate vibratory energy (e.g., ultrasonic energy) upon receiving a control signal to activate a weld cycle. In the exemplary embodiment, horn 480 is configured to transmit the vibratory energy to an operative site. More specifically, horn 480 is coupleable to end effector 490 such that the vibratory energy is transmitted to end effector 490 through horn 480. Alternatively, the vibratory energy may be transmitted to the operative site using any mechanism that enables handpiece 420 to function as described herein.

The embodiments described herein relate generally to medical devices and, more particularly, to an ultrasonic handpiece. The ultrasonic handpieces described herein enable monitoring forces and/or pressures applied to the handpiece, its components, and/or a surgical implement. As such, the handpieces described herein facilitate creating effective and/or reliable welds, thereby improving a repair, stabilization, and/or healing time associated with the patient.

Exemplary embodiments of ultrasonic handpieces are described above in detail. The methods and systems are not limited to the specific embodiments described herein, but rather, components of systems and/or steps of the method may be utilized independently and separately from other components and/or steps described herein. Each method step and each component may also be used in combination with other method steps and/or components. Although specific features of various embodiments may be shown in some drawings and not in others, this is for convenience only. Any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of operating a handheld medical device to form a weld at one or more surgical implements, said method comprising:
   detecting a first pressure applied to a transducer of the handheld medical device, wherein the first pressure is a result of a second pressure applied to a distal end of a horn of the handheld medical device when the distal end of the horn is pressed against the one or more surgical implements;
   transmitting a signal associated with the first pressure;
   generating vibratory energy when the first pressure is within a predetermined pressure range indicating that the second pressure at the distal end of the horn is suitable for forming the weld; and
   transferring, when the first pressure has settled within the predetermined pressure range for at least a predetermined settling interval, the vibratory energy through the horn to the one or more surgical implements to form the weld at the one or more surgical implements for stabilizing body tissue with the weld, the settling interval being a pre-programmed duration of time and initiated after the first pressure has been sensed within the predetermined pressure range allowing the pressure to settle within the predetermined pressure range, the transfer of vibratory energy being inhibited until the first pressure has settled within the predetermined pressure range for at least the predetermined settling interval, wherein the predetermined settling interval is 2 seconds.

2. The method of claim 1 further comprising restricting an inner housing from moving toward the transducer beyond a predetermined position, wherein the inner housing houses at least a portion of the horn.

3. The method of claim 1 further comprising counteracting the first pressure applied to the transducer.

4. The method of claim 1 further comprising coupling an end effector to the horn.

5. The method of claim 1 further comprising extending a sheath about the horn.

6. The method of claim 1 further comprising identifying the handheld medical device based on an identifier associated with the handheld medical device.

* * * * *